United States Patent [19]

Quinby

[11] 4,164,940

[45] Aug. 21, 1979

[54] DENTAL CLEANING AND MASSAGING APPARATUS

[76] Inventor: James D. Quinby, 1092 NE. Glass Dr., Jensen Beach, Fla. 33457

[21] Appl. No.: 865,867

[22] Filed: Dec. 30, 1977

[51] Int. Cl.² .............................................. A61H 7/00
[52] U.S. Cl. ................................... 128/62 A; 32/40 R
[58] Field of Search ........................... 128/87 R, 62 A; 32/40 R, 88

[56] References Cited

U.S. PATENT DOCUMENTS

| 3,527,218 | 9/1970 | Westline | 128/62 A |
| 3,908,642 | 9/1975 | Vinmont | 128/40 |
| 4,059,101 | 11/1977 | Richmond | 128/62 A |
| 4,106,501 | 8/1978 | Ozbey et al. | 128/62 A |

*Primary Examiner*—Robert Peshock

*Attorney, Agent, or Firm*—Witherspoon, Lane & Hargest

[57] ABSTRACT

Apparatus for cleaning teeth and the gingival crevices and for massaging the gums is disclosed. The apparatus comprising a mouthpiece having an upper channel member adapted to fit over at least a part of the upper dentation and to snugly engage the upper gum and a lower channel member adapted to fit over at least a part of the lower dentation and to snugly engage the lower gum. The upper and lower channels are joined by a membrane means which form fluid chambers. Pneumatic means are provided to move the upper and lower channel members upward and downward over the respective gums to massage the gums. In addition water or any suitable cleaning fluid is introduced into and out of the apparatus to clean the teeth and gingival crevices and to provide lubrication for the massaging action of the pneumatic means.

15 Claims, 5 Drawing Figures

DENTAL CLEANING AND MASSAGING APPARATUS

BACKGROUND OF THE INVENTION

This invention relates to dental apparatus and more specifically to dental cleaning and massaging apparatus.

Research has clearly shown that the brushing of teeth as commonly practiced does not provide adequate cleaning of the teeth and the area around the teeth to prevent caries and peridental disease. Toothpicks and dental floss have been used to augment brushing. However, even the use of toothpicks and/or dental floss in combination with brushing does not provide the cleaning necessary to adequately guard against caries and peridental disease.

In recent years hydro-therapy devices that provide a higher degree of cleansing, particularly cleansing of the gingival crevices, have been devised and introduced on the market. This invention provides for the hydraulic cleaning of the teeth of a person and at the same time provides for the massaging of the gums. Research has also shown that gentle non-damaging massaging of the gums promotes dental health.

SUMMARY OF THE INVENTION

The apparatus of this invention provides a relatively simple and highly effective means for cleaning teeth and the gingival crevices and for massaging the gums. The apparatus comprises a mouthpiece having upper and lower channel members that fit over the upper and lower teeth, respectively, and fit snugly against the respective gums. The channel members are joined by a membrane structure and pneumatic means are provided to move the upper and lower channel members relative to the upper and lower gums, respectively, to thereby massage the gums. Hydraulic means to clean the teeth and gingival crevices and to lubricate the gums during massaging are also provided.

BRIEF DESCRIPTION OF THE DRAWING

A complete and full understanding of the invention can be obtained from the following detailed description when read in conjunction with the annexed drawing in which.

DESCRIPTION OF THE INVENTION

Figure 3:
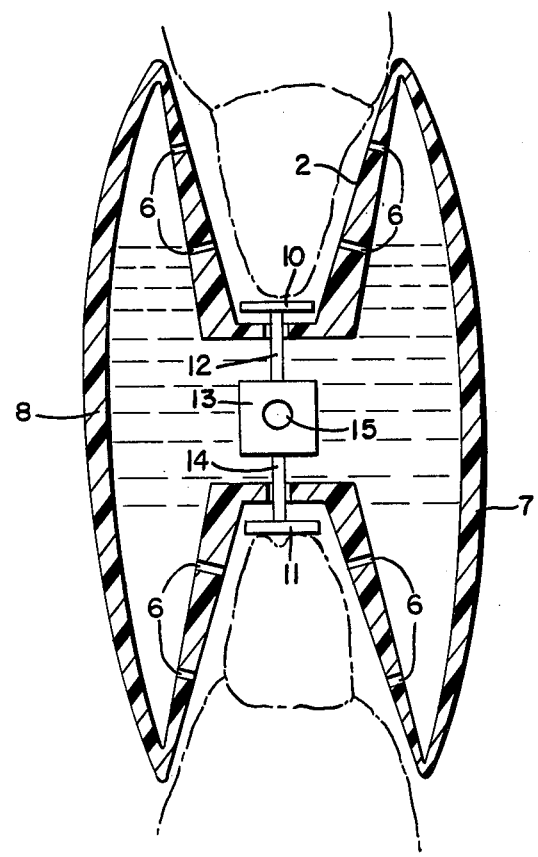
FIG. 3 is a cross-sectional view of the mouthpiece along the line 3—3 of FIG. 2.
Figure 4:
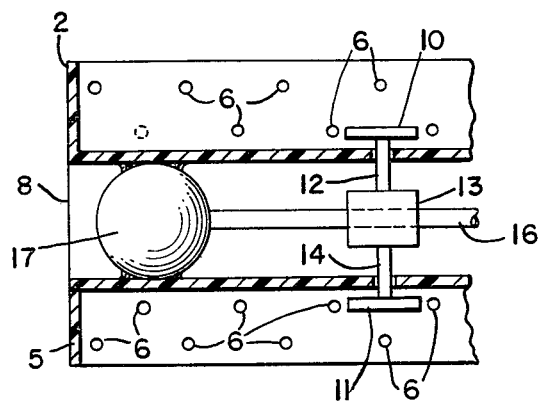
FIG. 4 is a cross-sectional view of the mouthpiece taken along the line 4—4 of FIG. 2 with the air-socks of the pneumatic means inflated.
Figure 5:
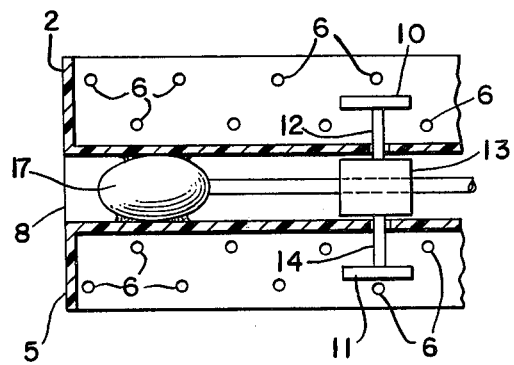
FIG. 5 is the cross-sectional view of FIG. 4 with the air-socks deflated.

Referring to the drawing, the invention comprises a mouthpiece 1 having an upper channel member 2 and a lower channel member 5 (FIGS. 3, 4 and 5). Upper channel member 2 is essentially identical to the upper mouthpiece worn by a boxer but modified according to this invention; and, similarly, lower channel member 5 is essentially identical to the lower mouthpiece worn by a boxer but modified according to this invention. This upper channel member 2 is designed to fit over the upper teeth of the user and to snugly fit against the upper gum and lower channel member 5 is designed to fit over the lower teeth of the user and to fit snugly against the lower gum. Upper channel member 2 and lower channel member 5 are made of a relatively soft but semi-rigid material. Holes 6 (see FIGS. 4, 5 and 6) are cut through both legs or sides of upper channel member 2 and lower channel member 5. The function of these holes will be described later herein.

A first or outer membrane 7 extends from upper channel member 2 downward to lower channel member 5 as is more clearly shown in FIG. 3. As shown in FIG. 3, outer membrane 7 is integrally formed with the uppermost part of upper channel member 2 at one end and is integrally formed with the lowermost part of lower channel member 5. Instead of being integrally formed with upper and lower channel members 2 and 5, respectively, outer membrane 7 can be and from a production standpoint preferably is secured by any suitable means such as a non-toxic adhesive at one end to upper channel member 2 and at its other end to lower channel member 5. A second or inner membrane 8 extends from the uppermost part of upper channel member 2 downward to the lowermost part of lower channel member 5 (see FIG. 3). Again, the top part of second membrane 8 is shown in FIG. 3 as being integrally formed with upper channel member 2 at one end and with lower channel member 5 at its other end but can be and preferably is secured to the uppermost part of upper channel member 2 at one end and to the lowermost part of lower channel member 5 at its other end by any suitable means and is a non-toxic adhesive. Outer membrane 7 and inner membrane 8 are conveniently made of a relative soft material that is somewhat elastic. From the foregoing description of outer member 7 and inner membrane 8, it is apparent that the area between the uppermost part of upper channel member 2 and the lowermost part of the lower channel member 5 is enclosed by means of membranes 7 and 8. Although it is not clearly visible in FIGS. 1 and 2, membranes 7 and 8 are brought around the back of upper and lower channel members 2 and 5 such that the closed area formed by membranes 7 and 8 is a sealed area.

A plurality of the bite blocks 10 are located in both upper and lower channel members 2 and 5. Three bite blocks 10 are shown in upper channel member 2. An identical number of bite blocks are located in lower channel member 5 directly below bite blocks 10. One of these bite blocks, the bite block 11, located in lower channel member 5 is shown in FIGS. 3, 4 and 5. Referring specifically to FIGS. 3, 4 and 5, a rod or post 12 has one end secured to or integrally fabricated with bite block 10. The other end of post or rod 12 is secured to or integrally fabricated with the block 13. A rod or post 14 has one end secured to or integrally fabricated with bite block 11 and its other end is integrally fabricated with or secured to block 13. A hole 15 is cut through block 13. All three bite block structures are identical. Thus, all three bite block structures comprise a bite block 10 in upper channel 2, a bite block 11 in lower channel 5, a post or rod 12, a block 13 having a hole 15 and a post or rod 14. While the number of bite block structures provided is not critical, it will be obvious later herein from the description of the operation that at least three bit block structures should be provided.

Figure 2:
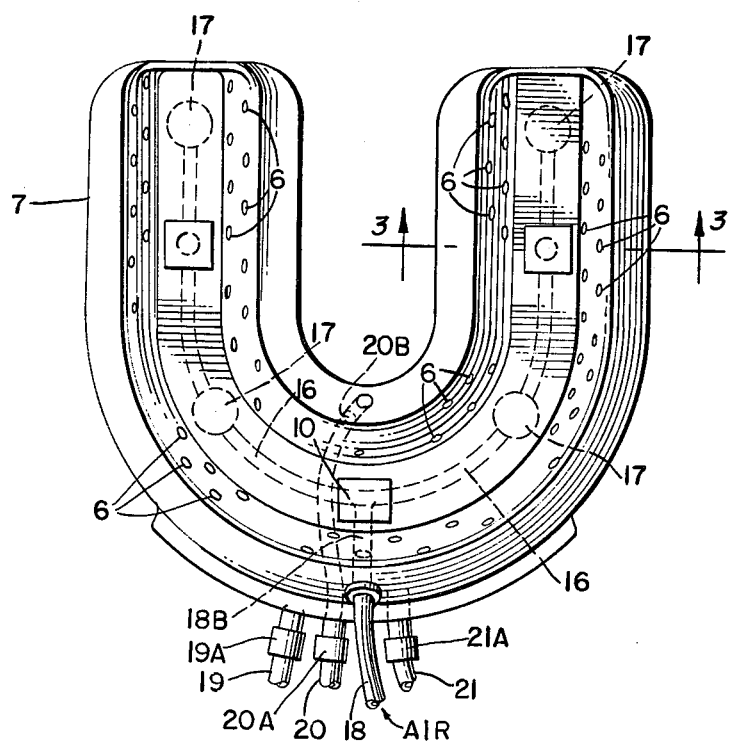
FIG. 2 is a top view of the mouthpiece of the invention.

A hose or tube 16 is positioned between the bottom of upper channel member 2 and the top of lower channel member 5. The hose or tube 16 is shaped to extend along the entire bottom and top surfaces of upper channel members 2 and 5, respectively, as is shown in FIG. 2. Hose or tube 16 is threaded through holes 15 of blocks 13 as shown in FIGS. 3, 4 and 5. A plurality of air-sacks 17 are integrally formed along tube or hose 16 as shown in FIG. 2. Conveniently, air-sacks 17 are areas formed along tube or hose 16 that are more elastic than the balance of hose 16 so that air-sacks 17 will expand when inflated by air while the balance of hose or tube 16 remains substantially unchanged when air-sacks 17 are inflated or deflated. While the number of air-sacks provided is not critical, four air-sacks located as shown in FIG. 2 is probably the minimum number required for satisfactory operation. More air-sacks 17 could be provided or for that matter the entire hose or tube 16 could be made of the same material as air-sacks 17 so that the entire tube or hose 16 would expand when inflated except, of course, in the area where hose or tube 16 passes through the holes 15 of blocks 13. Air-sacks 17 are secured to upper and lower channel members 2 and 5 by a suitable adhesive or the like.

Figure 1:
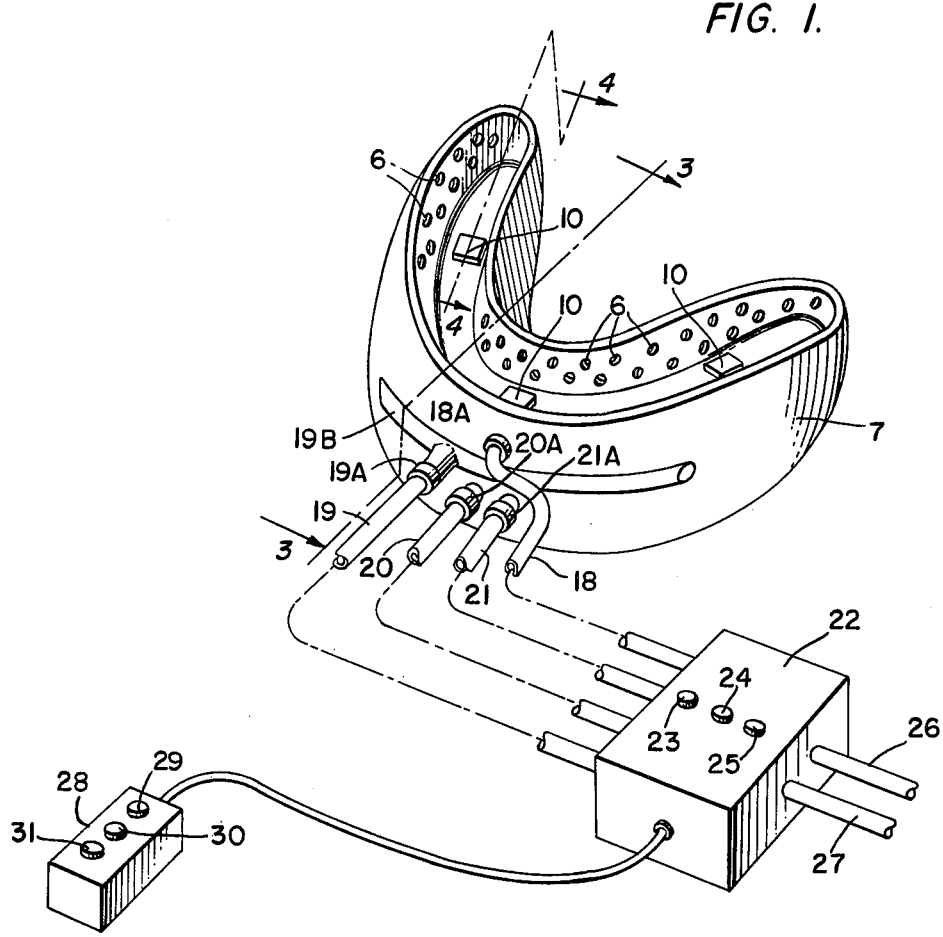
FIG. 1 is a pictorial representation of the invention.

Referring specifically to FIGS. 1 and 2, a hose or tube 18B has one end secured to or is integrally fabricated with hose 16. The other end of hose 18B is secured to the coupler 18A. Coupler 18A is secured to and passes through membrane 7 such that one end, the end secured to hose 18B, is located in the enclosed area formed by membranes 7 and 8 and the other end extends slightly beyond the outer surface of membrane 7. A hose or tube 19B is secured along the outside of membrane 7 as shown more clearly in FIG. 1. Both ends of tube 19B are open. A coupler 19A, one end of which communicates with the inside of hose 19B, is secured to hose 19B at approximately the mid-point of hose 19B. The other end of coupler 19A extends slightly beyond the outside surface of hose 19B.

A hose or tube 20B is located in the area formed by membranes 7 and 8. One end of hose 20B extends through membrane 8. This end of hose 20B conveniently and preferably is flush with the outside surface of membrane 8. The other end of hose 20B is secured to one end of the coupler 20A. Coupler 20A is secured to membrane 7 such that one end of coupler 20A, the end secured to hose 20B, is located in the area formed by membranes 7 and 8 and the other end extends slightly beyond the outside surface of membrane 7.

A coupler 21A is secured to membrane 7 such that one end of coupler 21A extends into the enclosed area formed by membranes 7 and 8 and the other end extends slightly beyond the outer surface of membrane 7. Seals are provided around couplers 18A, 20A and 21A where they pass through membrane 7 so that a fluid tight seal is provided between membrane 7 and each of the couplers 18A, 20A and 21A. Similarly, a seal is provided between hose 19B and the area adjacent the end of coupler 19A that communicates with the inside of hose 19B so that a fluid tight seal is provided between hose 19B and this end of coupler 19A.

One end of each of the hoses or tubes 18, 19, 20 and 21 is coupled to a control box 22. The other end of hoses 18, 19, 20 and 21 are coupled to couplers 18A, 19A, 20A and 21A, respectively. The end of each of the hoses 18, 19, 20 and 21 that is coupled to its mating coupler 18A, 19A, 20A and 21A, respectively, is preferably provided with a mating connector, not shown in the drawing, such that hoses 18, 19, 20 and 21 can be quickly coupled to and uncoupled from couplers 18A, 19A, 20A and 21A, respectively. Any type of suitable well known quick connect and disconnect coupling arrangement can be used to couple hoses 18, 19, 20 and 21 to their respective couplers. In addition to quick disconnect, the couplers permit one control unit 22 to be used interchangeably with a plurality of mouthpieces. Three ON-OFF switches, the switches 23, 24 and 25, are provided on control box 22. The outlet hoses 26 and 27 have one end coupled to control box 22. Control box 22 is provided with a remote control device 28 that is sized and shaped to be conveniently held in the hand of the user of the apparatus of this invention. Remote control device 28 is provided with the switches 29, 30 and 31.

The apparatus of this invention operates as follows: The user inserts mouthpiece 1 into his or her mouth such that upper channel member 2 fits over the upper teeth and snugly against the upper gum and lower channel 5 fits over the lower teeth and snugly against the lower gum. Control box 22 is then activated to provide either air pulses and water or air pulses alone or water alone. The air pulses are provided to air-sacks 17 from control box 22 through hose 18, coupler 18A, hose 18B and hose 16. Control box 22 is provided with an air pump that operates cyclically to alternately provide pulses of air with periods of no air between the air pulses. When air pulses are provided, air-sacks 17 are inflated and during the period between air pulses air-sacks 17 are deflated. The elasticity of air-sacks 17 and the elasticity of membranes 7 and 8 forces the air out of air-sacks 17 through hose 16, hose 18B, coupler 18A and hose 18 during the period between air pulses. Instead of relying solely on the elasticity of air-sacks 17 to drive out the air, the pump of control box 22 could alternately pump air in and such air out; thereby ensuring positive inflation and deflation of air-sacks 17. In any event, control box 22 must operate such that air-sacks 17 are alternately inflated and deflated.

Referring to FIGS. 4 and 5, FIG. 4 shows a single air-sack 17 in its inflated condition and FIG. 5 shows an air-sack 17 deflated. All of the air-sacks 17 are inflated or deflated at the same time. When the air-sacks 17 are inflated, upper channel member 2 rides up on the upper gum and lower channel member 5 rides down on the lower gum. When air-sacks 17 are deflated, the upper channel member 2 will ride down on the upper gum and lower channel member 5 will ride up on the lower gum. Thus, as air-sacks 17 are inflated and deflated, upper and lower channel members 2 and 5 provide a massaging action on the gums. The teeth are held in place by the bite blocks 10 and 11 so that the upper and lower channel members 2 and 5 will ride up and down on the gums with the teeth staying in place. The elasticity of the membranes and the air-sacks pulls upper and lower channel members toward each other when air-sacks 17 are deflated.

At the same time that control box 22 is providing air to massage the gums, control box 22 also provides a source of water and/or cleaning fluid through hose 21 and coupler 21A into the area formed by membranes 7 and 8. This water and/or cleaning fluid flows through holes 6 in upper and lower channel members 2 and 5 to clean and flush out the teeth and gums. This fluid is preferably introduced into mouthpiece 1 as a gentle steady stream. In addition to providing a cleaning action, the fluid serves as a lubricant during the massaging action.

Since some fluid will seep out between the gums and upper and lower channel members 2 and 5, suction hose 9 is provided on the outside of membrane 7. Suction hose 9 is coupled to control box 22 by means of coupler 19A and hose 19. Control box 22 sucks any fluid seepage out of the mouth of the user through hose 9, coupler 19A and hose 19. Similarly, hose 20B serves as a suction hose to suck out the fluid that seeps into the area of the mouth outside of inner membrane 8. This seepage is drawn out by control box 22 through hose 20B, coupler 20A and hose 20.

A source of water is provided to control box 22 by means of the hose 26. This water can be mixed with a cleaning fluid that is stored inside of control box 22. If no cleaning fluid is to be used, no such fluid will be stored in control box 22. Similarly, if only cleaning fluid is used, the source of water is cut off. Also, a mixture of water and cleaning fluid can be stored in control box 22 and hose 26 eliminated, if control box 22 is provided with a sufficiently large storage compartment for the fluid. The fluid drawn out of the mouth around mouthpiece 1 through hoses 19 and 20 is drained out of control box 22 by means of hose 27. If a drain pan is provided in control box 22, hose 27 can be eliminated.

While under most circumstances, the apparatus will be used with both cleaning fluid and with air to provide the massaging action, the apparatus can be operated such that either air only is provided or cleaning fluid only is provided, or both air and cleaning fluid are provided. Control box 22 is provided with three ON-OFF switches to provide the three modes of operation. For example, switch 23 would provide both air and water, switch 24 air only and switch 25 water only.

While the apparatus can be operated from control box 22, a remote control device 28 is preferably provided. Remote control device 28 is of such size and shape that it is easily hand held and is provided with switches 29, 30 and 31 that correspond in operation to switches 23, 24 and 25, respectively. Alternately, remote control device 28 can be and preferably is provided with a single ON-OFF pushbuttom switch with the mode of operation set by switches 23, 24 and 25. This single switch or remote control device 28 would then operate to merely activate the control box 22.

While the invention has been described with reference to a specific embodiment, it will be obvious to those skilled in the art that various changes and modifications can be made to this embodiment without departing from the spirit and scope of the invention as set forth in the claims. For example, bristles can be added to the upper and lower channels to assist the massaging action and a single coupling arrangement could be used to couple the control panel to the mouthpiece.

I claim:

1. Dental hygiene apparatus comprising:
   a mouthpiece having a generally U-shaped upper channel member open at the top and a generally U-shaped lower channel member open at the bottom;
   a first membrane and a second membrane, said first and second membranes each being secured to said upper and lower channel members such that a closed area is formed between said first and second membranes;
   a plurality of inflatable air-sacks located inside said closed area, adjacent to the bottom surface of said upper channel member and adjacent the upper surface of said lower channel member such that said plurality of air-sacks are located between said upper and lower channel members;
   a first plurality of bite blocks located in said upper channel member, said first plurality of bite blocks being spaced apart in said upper channel member;
   a second plurality of bite blocks equal in number to said first plurality of bite blocks, said second plurality of bite blocks being so located in said lower channel member such that each one of said second plurality of bite blocks is located directly opposite a different one of said first plurality of bite blocks;
   a plurality of connecting posts equal in number to the number of said first and second plurality of bite blocks, one end of each of said connecting posts being secured to a different one of said first plurality of bite blocks and the other end of each one of said plurality of connecting posts being secured to a different one of said second plurality of bite blocks; and
   means for periodically inflating said plurality of air-sacks such that said plurality of air-sacks are alternately inflated and deflated to cause said upper and lower channel members to alternately move away from and toward each other.

2. The dental hygiene apparatus as defined in claim 1 wherein said generally U-shaped upper and lower channel members each contain a plurality of holes, said holes communicating with said closed area formed by said first and second membranes and wherein means are provided for introducing a cleaning and lubricating fluid into said closed area.

3. The dental hygiene apparatus as defined in claim 2 wherein a first hose, open at both ends, is secured to the outer surface of said first membrane and wherein means are coupled to said first hose for withdrawing any of said cleaning and lubricating fluid that may be present in the area adjacent the outer surface of said first membrane.

4. The dental hygiene apparatus as defined in claim 3 wherein a second hose is located inside said closed area, one end of said second hose communicating with the area adjacent to the outside surface of said second membrane and the other end of said second hose communicating with the outside of said first membrane and wherein means are coupled to said second hose for withdrawing any of said cleaning and lubricating fluid present in the area adjacent the outside surface of said second membrane.

5. The dental hygiene apparatus as defined in claim 4 wherein said plurality of air-sacks are interconnected by means of a first air hose and wherein said first air hose is coupled to one end of a second air hose and wherein the other end of said second air hose is coupled to said means for periodically inflating said air-sacks.

6. The dental hygiene apparatus as defined in claim 5 further including a control box and further including means for coupling said control box to said first hose, to said second hose, to said second air hose and to said means to introduce cleaning and lubricating fluid into said closed area.

7. The dental hygiene apparatus as defined in claim 6 wherein said means to periodically inflate said air-sacks comprises a source of air coupled to said second air hose, said source of air being located in said control box.

8. The dental hygiene apparatus as defined in claim 7 wherein said means for introducing said cleaning and lubricating fluid into said closed area includes fluid passage means having a first and second end, said first end of said fluid passage means passing through said first membrane such that said first of said fluid passage means is in said closed area with said second end of said fluid passage means being extended beyond the outer surface of said first membrane and wherein a fluid hose has one end coupled to said second end of said fluid passage means and its other end coupled to said control box and wherein said control box includes means for providing a source of cleaning and lubricating fluid.

9. The dental hygiene apparatus as defined in claim 8 wherein a first suction hose has one end coupled to said first hose and its other end coupled to said control box and wherein a second suction hose has one end coupled to said second hose and its other end coupled to said control box and wherein said control box includes means for drawing said cleaning and lubricating fluid into said control box through said first and second hoses and said first and second suction hoses.

10. The dental hygiene apparatus as defined in claim 9 wherein said fluid passage means comprises a first quick disconnect coupler having a first end located in said closed area and having a second end located beyond the outer surface of said first membrane, said second end of said first quick disconnect coupler being coupled to said one end of said fluid hose.

11. The dental hygiene apparatus as defined in claim 10 wherein said means to couple said source of air to said second air hose comprises a third air hose having one end coupled to said second air hose and having its other end coupled to said control box.

12. The dental hygiene apparatus as defined in claim 11 further including a second and third quick disconnect coupler, each having a first end and second end, said first end of said second quick disconnect coupler being located in said closed area and being coupled to said second air hose, said first end of said third quick disconnect coupler being located in said closed area and being coupled to said one end of said second hose, said second end of said second quick disconnect coupler being located beyond the outside surface of said first membrane and being coupled to said third air hose and said second end of said third quick disconnect coupler being located slightly beyond said outer surface of said first membrane and being coupled to said one end of said second suction hose.

13. The dental hygiene apparatus as defined in claim 12 further including a fourth quick disconnect coupler secured to said first hose, said fourth quick disconnect coupler having a first end communicating with the inside of said first hose and having a second end coupled to said one end of said first suction hose.

14. The dental hygiene apparatus as defined in claim 13 wherein said control box includes operative means for selectively providing air to said third air hose, cleaning and lubricating fluid to said fluid hose, one at a time and for providing air to said third air hose and cleaning and lubricating fluid to said fluid hose simultaneously.

15. The dental hygiene apparatus as defined in claim 14 further including remote control means coupled to said control box for operating said control box.

* * * * *